US005629281A

United States Patent [19]
Butler

[11] Patent Number: 5,629,281
[45] Date of Patent: May 13, 1997

[54] HERBEL MEDICATION FOR EXTERNAL APPLICATION

[76] Inventor: Edward R. Butler, 213 Huguenot St., New Paltz, N.Y. 12561

[21] Appl. No.: 630,036

[22] Filed: Apr. 2, 1996

Related U.S. Application Data

[63] Continuation of Ser. No. 325,534, Oct. 18, 1994, abandoned, which is a continuation of Ser. No. 944,346, Sep. 14, 1992, abandoned.

[51] Int. Cl.$^6$ ............................. A01N 61/02; A61K 9/70
[52] U.S. Cl. .................. 514/1; 514/844; 514/938; 424/449
[58] Field of Search ........................ 514/844, 938; 424/449

[56] References Cited

PUBLICATIONS

Pharmaceutical Formulas, 12th ed., 1953, pp. 505, 535–540, 671, 649, 677, 852 and 853.

Martindale, The Extra Pharmacopoeia, 22nd ed., vol. I, 1941, pp. 739–741, 990, 991, 998, 742.

Cosmetic Dermatology, 1936, Goodman, pp. 73, 77–79, 81, 83, 76.

Pharmaceutical Formulas, Jan. 1947, vol. II, 10th ed., pp. 190, 191, 196, 197, 356–359.

*Primary Examiner*—Shelley A. Dodson
*Assistant Examiner*—Michael A. Williamson
*Attorney, Agent, or Firm*—Jordan B. Bierman; Bierman and Muserlian

[57] ABSTRACT

Applied externally, the preparation, composed of a mixture of herbal oils, relieves pain associated with various types of minor headaches. The preparation is also a solvent. The ingredients include the oils of lemon, sweet almond, cajuput, clove, eucalyptus, peppermint and thyme in specific proportions. All ingredients are natural.

18 Claims, No Drawings

HERBEL MEDICATION FOR EXTERNAL APPLICATION

This application is a continuation of application Ser. No. 08/325,534, filed Oct. 18, 1994, now abandoned, which is a continuation of application number 07/944,346, filed Sep. 14, 1992, now abandoned.

The present invention relates to a medical preparation applied externally to relieve minor headache pain, and to transfer medicines through the skin to the blood stream. The invention relates more particularly to such a preparation which is composed of all naturally occurring ingredients.

Headaches, major and minor, are probably the most common type of pain and are believed to be the number one cause of absenteeism in the work place. However, minor headaches are not a sign of serious disorder. The pain does not originate in the brain itself but instead commonly arises in the meninges (the membranes which envelope the brain and spinal cord) or in the blood vessels and muscles of the scalp.

The pain is believed to be a result of tension in or stretching (construction and dilation) of these tissues. Application of my preparation to the underside of both wrists, or to the scalp, proximate to the affected area, soothes the distressed tissues and vessels causing relief of the pain. The preparation does not cure the cause of the headache. It only takes away the associated pain.

Topical application of the preparation provides a means for transmission of medicine directly to the blood stream. Thus, my preparation is a natural transdermal vehicle and can be used to transfer additional medicines as well.

It has also been found that external application of the preparation to the underside of both wrists, where blood vessels are near the skin surface, will permit sufficient quantities of the medication to enter the blood stream. The medication is then carried through the blood vessels to the head area, relieving the pain.

Application to the underside of the wrists works as a preventative if the preparation is used on a regular basis i.e., once every five (5) days. The preparation also prevents most minor headache recurrences and lessens their pain. It relieves the pain associated with vessel trauma, as well.

I have found that my preparation works extremely fast. For example, when applied to the scalp, relief is reported to take place in about 2 to 3 seconds. Application to the wrist takes slightly longer, in the order of minutes.

There are many types of headaches, often described as migraine, stress, cluster, sleep disorder, alcohol related, PMS, tension, etc. I believe my preparation to be equally effective in relieving all types of minor headaches.

Moreover, my preparation includes only naturally occurring ingredients. Although each of the ingredients has been known individually for years, I believe that unexpected results are achieved by the combination of these ingredients in proper proportion.

It is, therefore, a prime object of the present invention to provide a medical preparation for external use capable of quickly relieving the pain associated with minor headaches of various types.

It is a further object to provide a (minor) headache preventative as well as a reliever of vessel trauma.

It is still a further object to provide a preparation which reduces the severity and length of any recurring headache and is a vehicle for transmission of medications, when applied topically, to the blood stream.

It is another object to formulate such a medication from naturally occurring ingredients.

In general, these objects are achieved by a preparation which is composed of a mixture of naturally occurring herbal oils. The herbal oils of lemon, sweet almond, cajuput, clove, eucalyptus, peppermint and thyme are provided in specified proportions.

The preparation is intended to be applied externally. One preferred method of application is by means of a foil-enclosed cotton applicator containing the preparation. The applicator contents are wiped on the skin underneath both wrists. Alternatively, the applicator contents are wiped on the scalp at the pain's site. This allows the transfer of the preparation through the skin to the blood stream.

More specifically, the preferred embodiment of the preparation of the present invention includes a mixture of approximately 10% lemon oil, 16% sweet almond oil, 9% cajuput oil, 14% clove oil, 16% eucalyphis oil, 20% peppermint oil and 15% thyme oil. All proportions are specified on a volume basis. While these proportions are believed to be best at this time, further experimentation may reveal that somewhat different proportions may perform satisfactorily as well.

The most preferred embodiment of the medication of the present invention includes a mixture of 10.135% lemon oil, 16.216% sweet almond oil, 8.784% cajuput oil, 13.851% clove oil, 16.216% eucalyptus oil, 19.595% peppermint oil and 15.203% thyme oil. These proportions constitute the most preferred composition known to me at this time.

While only a single preferred embodiment of the present invention has been described for purposes of illustration, it should be obvious that the proportions of the ingredients may vary. It is intended to cover all variations of the composition which fall within the scope of my invention, as defined by the following claims:

I claim:

1. A preparation for external application consisting essentially of amounts of lemon oil, sweet almond oil, cajuput oil, clove oil, eucalyptus oil, peppermint oil and thyme oil effective to reduce pain of headaches.

2. The preparation of claim 1 wherein the lemon oil comprises approximately 10%.

3. The preparation of claim 2 wherein said lemon oil comprises 10.135%.

4. The preparation of claim 1 wherein the sweet almond oil comprises approximately 16%.

5. The preparation of claim 4 wherein the sweet almond oil comprises 16.216%.

6. The preparation of claim 1 wherein cajuput oil comprises approximately 9%.

7. The preparation of claim 6 wherein cajuput oil comprises 8.784%.

8. The preparation of claim 1 wherein the clove oil comprises approximately 14%.

9. The preparation of claim 8 wherein the clove oil comprises 13.851%.

10. The preparation of claim 1 wherein the eucalyptus oil comprises approximately 16%.

11. The preparation of claim 10 wherein the eucalyptus oil comprises 16.216%.

12. The preparation of claim 1 wherein the peppermint oil comprises approximately 20%.

13. The preparation of claim 12 wherein the peppermint oil comprises 19.595%.

14. The preparation of claim 1 wherein the thyme oil comprises approximately 15%.

15. The preparation of claim 14 wherein the thyme oil comprises 15.203%.

16. A medical preparation for external application consisting essentially of 10.135% lemon oil, 16.216% sweet almond oil, 8.784% cajuput oil, 13.851% clove oil, 16.216% eucalyptus oil, 19.595% peppermint oil and 15.203% thyme oil.

17. A method of reducing pain of headaches comprising topically applying a preparation of claim 1 to human skin.

18. A method of transdermally administering medicine to the human body which comprises topical application of a preparation consisting essentially of effective amounts of lemon oil, sweet almond oil, cajuput oil, clove oil, eucalyptus oil, peppermint oil and thyme oil, also containing said medicine, to human skin.

* * * * *